United States Patent [19]

Cipris et al.

[11] 4,069,259
[45] Jan. 17, 1978

[54] PROCESS FOR PREPARING ORGANIC DISULFIDES

[75] Inventors: Divna Cipris, Morristown, N.J.; Dirk Pouli, Williamsville, N.Y.

[73] Assignee: Allied Chemical Corporation, Morris Township, N.J.

[21] Appl. No.: 733,727

[22] Filed: Oct. 19, 1976

[51] Int. Cl.$^2$ .................. C07C 149/12; C07D 277/78; C07D 263/58; C07D 235/28

[52] U.S. Cl. .................................. 260/608; 260/306.5; 260/307 D; 548/327; 548/328; 548/329

[58] Field of Search ............. 260/307 D, 309.2, 306.5, 260/608; 548/305

[56] References Cited

U.S. PATENT DOCUMENTS 3,072,707 1/1963 Pierson et al. ...................... 260/608

OTHER PUBLICATIONS

L. Field, JACS 74, 394, (1952).
D. Gibson et al., J. Chem. Soc. 127, 1821, (1925).

*Primary Examiner*—Joseph Paul Brust
*Assistant Examiner*—Molly C. Eakin
*Attorney, Agent, or Firm*—Robert J. North; Jay P. Friedenson

[57] ABSTRACT

A process is described for preparing organic disulfides, useful as accelerators in vulcanization and as anti-oxidants for synthetic rubber latexes, which comprises reacting an organic sulfonyl halide with a mercaptan in a ratio of at least about 5 moles of mercaptan per mole of sulfonyl halide, wherein by-product sulfinic acid is not formed in the final product.

11 Claims, No Drawings

PROCESS FOR PREPARING ORGANIC DISULFIDES

BACKGROUND OF THE INVENTION

1. Field of the Invention

This invention relates to a new and improved process for preparing organic disulfides from organic sulfonyl halides and mercaptans.

2. Brief Description of the Prior Art

Disulfides are extensively used in the area of polymerization technology. They are used as accelerators in vulcanization, as anti-oxidants and stabilizers for synthetic rubber latexes, as softeners for reclaimed vulcanizates, as intermediates in the manufacture of pigments and insecticides, and as agents for improving the properties of fuel and lubricating oils.

The conventional prior art method for producing organic disulfides involves the oxidation of mercaptans and possesses the disadvantage of requiring expensive and/or hazardous oxidizing agents, such as peroxides or iodine.

Another methd used to prepare disulfides involves reacting a sodium or potassium disulfide with an alkyl halide which has the disadvantage of forming impurities which are difficult to remove. Still another method involves the reaction of highly toxic sulfenyl halides with mercaptans.

Disulfides can also be produced by reduction of organic sulfur-oxygen containing compounds containing sulfur in a higher valence state, such as sulfonyl halide, or thiosulfonates. One such procedure involves th electrochemical reduction of sulfonyl halides, particularly sulfonyl chlorides, to disulfides utilizing a mercury cathode. However, the use of this procedure is not attractive since it tends to lead to mercury pollution of streams and waters and requires expensive equipment and is not well suited to a batch type of process in a plant operation.

Mercaptans, also known as thiols, are known reducing agents in the art for organic sulfur-oxygen containing compounds, as exemplified in Field, JACS 74, 394 (1952) in which aromatic sulfonic acid anhydrides reduced by mercaptans yielding mixtures of thiosulfonates and disulfides.

It is also known in the art that when sulfonyl chlorides are reacted with mercaptans in a ratio of 2 moles of mercaptan per mole of sulfonyl chloride, a mixture of the corresponding sulfinic acid and disulfide is obtained, as exemplified in Gibson, Miller and Smiles, J. Chem. Soc. 127, 1821 (1925). The above reference also discloses that when thiosulfonates (disulphoxides) are reacted with mercaptans in a ratio of 1 mole mercaptan per mole of thiosulfonate, a mixture of sulfinic acid and disulfide is formed. It would appear in light of the prior art that sulfinic acid is a stable by-product in reduction of organic sulfur-oxygen containing compounds using mercaptans.

Thus, the prior art does not provide any process whereby sulfonyl chlorides may be reacted with mercaptans to produce disulfides in high yield and purity, free of by-product sulfinic acid.

SUMMARY

In accordance with the present invention, organic disulfides are produced in high yield and high purity free of by-product sulfinic acid by a process which comprises reacting an organic sulfonyl halide with a mercaptan in ratio of at least about 5 moles of mercaptan per mole of organic sulfonyl halide.

Although we do not wish to be bound by any theory, the reaction is believed to proceed in accordance with the following equation:

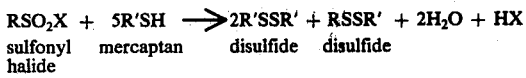

$$RSO_2X + 5R'SH \longrightarrow 2R'SSR' + RSSR' + 2H_2O + HX$$
sulfonyl halide    mercaptan    disulfide    disulfide where X is a halogen and R and R' can be the same or different and are organic radicals selected from the group consisting of: linear or branched alkyl radicals containing 1 to 18 carbon atoms; substituted benzyl radicals of the formula:

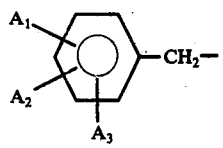

wherein substitutents $A_1$, $A_2$ and $A_3$ are independently selected from hydrogen, halogen and alkoxy containing 1 to 4 carbon atoms; cycloaliphatic radicals containing 5 to 8 carbon atoms and 0 to 2 chlorine atoms; aromatic radicals of the formula:

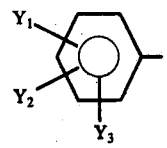

wherein $Y_1$, $Y_2$ and $Y_3$ are independently selected from hydrogen, halogen, alkyl containing 1 to 12 carbon atoms, alkoxy containing 1 to 4 carbon atoms, phenyl and a fused benzene ring formed from two adjacent Y substituents; and heterocyclic radicals of the formula:

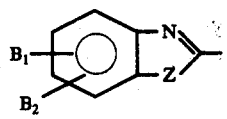

wherein Z is either oxyen, nitrogen or sulfur, and $B_1$ and $B_2$ are independently selected from hydrogen, halogen and alkoxy containing 1 to 4 carbon atoms.

Where R and R' are the same, three moles of the same disulfide are formed, and where R and R' are different, a mixture of disulfides is formed.

This reaction can be carried out in the presence of a polar solvent in which the organic sulfonyl halide and mercaptan are soluble or can be conducted neat in a liquid state in the presence of basic catalyst, preferably an organic amine.

DETAILED DESCRIPTION OF THE INVENTION AND THE PREFERRED EMBODIMENTS

The advantages of the process of this invention over the prior art are the preparation of organic disulfides in high yield and purity in the absence of by-product sulfinic acid which does not require metal electrodes, or expensive and/or hazardous oxidizing reagents or highly toxic starting materials and which incorporates the reagents used in the reaction into the final product. The products of the invention are either symmetrical or unsymmetrical organic disulfides generally containing 2 to 40 carbon atoms.

In general, mercaptans containing an R' group as defined above can be used, and the term mercaptan refers to an organic molecule containing the —SH group generally referred to as the mercapto, thiol or sulfhydryl group.

Alkyl or aliphatic mercaptans useful in the present invention include those which contain 1 to 18 carbon atoms and are linear or branched, including secondary and tertiary types.

Representative examples of linear aliphatic mercaptans are methyl-, ethyl-, propyl-, butyl-, decyl-, dodecyl-, an octadecylmetcaptan. Examples of branched mercaptans are isopropyl-, secondary butyl-, tertiary butyl- and tertiary dedeocylmercaptan.

Representative examples of substituted benzyl mercaptans are benzyl-, p-bromobenzyl-, p-chlorobenzyl-, p-methoxybenzyl-, 2,4-dichlorobenzyl-, 2,4,5-trichlorobenzyl-, 3,4,5-trimethoxybenzyl-, p-ethoxybenzyl- and p-butoxy-benzylmercaptan.

Representative examples of cycloaliphatic mercaptans are cyclopentyl-, cyclohexyl-, methylcyclohexyl-, ethylcyclohexyl-, 2-chlorocyclohexyl- and 2,4-dichlorocyclohexylmercaptan. Preferred among the general classes of aliphatic mercaptans discussed above are those containing 6 to 14 atoms.

Aromatic mercaptans, usually referred to as aromatic thiols or thiophenols, are also applicable in the present invention. In general, they contain 6 to 20 carbon atoms, and it is preferred to use those containing 6 to 10 carbon atoms.

Representative examples of aromatic mercaptans are benzene-, p-tolyl-, p-bromobenzene-, p-chlorobenzene-, p-methoxybenzene-, p-butoxybenzene-, 2,4-dichlorobenzene-, 2,5-dichlorobenzene-, p-dodecylbenzene-, p-phenyl-, 2,3,6-trichlorobenzene-, 2,4-dimethylbenzene-, 1-naphthalene-, and 2-naphthalenethiol. Among the aromatic mercaptans or thiols, a particularly preferred embodiment is 2,5-dichlorobenzenethiol.

Representative examples of heterocyclic mercaptans which are useful in the disclosed invention are 2-mercaptobenzimidazole, 2-mercaptobenzothiazole, 2-mercaptobenzoxazole, 5-chloro-2-mercaptobenzothiazole, 5-chloro-2-mercaptobenzoxazole, 5-chloro-2-mercaptobenzimidazole, and 5-methoxy-benzoxazole. A preferred embodiment is 2-mercapto-benzothiazole.

The organic sulfonyl halides that are useful in the present invention are the sulfonyl iodides, bromides or chlorides, but it is preferred to use the sulfonyl chlorides.

The organic sulfonyl halides useful in the disclosed invention have the same organic radicals as defined for the mercaptans, and generally contain 1 to 20 carbon atoms.

Representative examples of aliphatic sulfonyl halides are methane-, decane-, dodecane- and octadecanesulfonyl chloride. Representative examples of cycloaliphatic sulfonyl halides are cyclohexanesulfonyl chloride, cyclopentanesulfonyl chloride, 2-methylcyclopentanesulfonyl chloride and 2-chlorocyclopentanesulfonyl chloride.

Representative examples of substituted benzyl mercaptans, also named -toluenesulfonyl chlorides, are -toluenesulfonyl chloride, 4-chloro-, 4-bromo, 4-methoxy-, 4-butoxy, 2,4-dichloro-, 2,4-dimethoxy- and 3,4,5-trimethoxy- -toluenesulfonyl chloride.

Representative examples or aromatic sulfonyl halides are those containing a benzene or naphthalene nucleus, such as benzene-, para-toluene-, para-methoxy-benzene-, para-chlorobenzene-, para-butoxybenzene-, para-phenylbenzene-, p-dodecylbenzene 2,5-dichlorobenzene-, 2,4,5-trichlorobenzene-, xylene-, 1-naphthalene- and 2-naphthalenesulfonyl chloride. Preferred among the aromatic sulfonyl halides are the benzenesulfonyl chlorides containing 6 to 10 carbon atoms and in particular 2,5-dichlorobenzenesulfonyl chloride.

Representative examples of heterocyclic sulfonyl chlorides are benzimidazole-2-sulfonyl chloride, benzoxazole-2-sulfonyl chloride, benzothiazole-2-sulfonylchloride, 5-chlorobenzothiazole-2-sulfonyl chloride and 5-methoxybenzothiazole-2-sulfonyl chloride.

Symmetrical or unsymmetrical organic disulfides can be prepared by the process of this invention. It is preferred however, to produce symmetrical disulfides since a mixture of disulfides requires additional processing for their separation. Such methods of separation, however, should be obvious to one skilled in the art and include fractional distillation and fractional crystallization techniques.

The molar of mercaptan to sulfonyl halide employed in the process of this invention must be at least about 5 to 1. By use of such molar ratio, no detectable sulfinic acid will be present in the final reaction mixture, which is in marked contrast to the prior art processes where sulfinic acid is invariably formed. It is preferred that only about a 1 to 4 percent excess (over 5 moles) of mercaptan be employed in order to insure high conversion of the sulfonyl halide to disulfide. A larger excess of mercaptan can be used but is not necessary since it does not increase the efficiency or yield of the reaction.

The solvents which are useful in the present invention are polar organic and inorganic solvents which generally contain nitrogen and/or sulfur and/or oxygen, are effective solvents for the organic sulfonyl halide and mercaptans, and are inert under the conditions of the reaction. Examples of solvents that may be used are halogenated aliphatic hydrocarbons containing 1 to 4 carbon atoms such as carbon tetrachloride, tetrachloroethane and dichlorobutane; halogenated olefinic hydrocarbons containing 2 to 4 carbon atoms such as chlorobutadiene an perchloroethylene; halogenated aromatic hydrocarbons containing 6 to 10 carbon atoms such as chlorobenzene, an chloronaphthalene; ketones containing 3 to 6 carbon atoms such as acetone, butanone and methylisobutyl ketone; aromatic hydrocarbons containing 6 to 10 carbon atoms such as toluene, benzene and naphthalene; linear and cyclic aliphatic ethers containing 2 to 8 carbon atoms such as butyl ether and tetrahydrofuran; carboxylic acids containing 1 to 4 carbon atoms such as acetic, butyric and trichloroacetic acids; mineral aqueous acids such as 85 percent phosphoric acid; lower alkyl glycols containing 2 to 4 carbon atoms such as ethylene glycol and butylene glycol; polyethylene glycol; trialkylphosphites containing 3 to 15 carbon atoms such as tributylphosphite and tripentylphosphite; monohydric aliphatic alcohols containing 1 to 8 carbons such as methanol, ethanol, isopropanol and octanol; monoalkoxyethanols containing 3 to 6 carbon atoms such as methoxyethanol, ethoxyethanol and butoxyethanol; linear and cyclic alkylene sulfones containing 1 to 8 carbons such as tetramethylene sulfone and dibutylsulfone; lower aliphatic amides containing 1 to 4 carbon atoms such as formamide and butyramide; N,N-dialkylalkanoylmides containing 1 to 4 carbon atoms such as dimethylformamide and dimethylacetamide, and N-alkyl cyclic lactams containing 1 to 6 carbon atoms such as N-methyl- and N-ethylpyrrolidone.

The amount of solvent used is based on the molar ratio of solvent to sulfonyl halide and is generally in the range of 5 to 1 moles solvent per mole of sulfonyl halide with a preferred range being of about 3 to 1 moles solvent per mole of sulfonyl halide. The yields of disulfide are to some extent dependent upon the polarity of the solvent employed in addition to the molar ratio of solvent to sulfonyl halide. In general, the more strongly polar solvents such as ethanol, sulfolane and N,N-dimethylformamide give higher yields than less polar solvents such as benzene, toluene or chlorobenzene. A molar ratio of solvent to sulfonyl halide of at least about two is preferred for obtaining higher yields with a particular solvent used.

When the organic sulfonyl halide and mercaptan reactants are either liquids or low melting solids, the reaction can be conducted neat in the absence of a solvent. When the reaction is conducted neat, the reaction should be carried out in the liquid phase in the presence of a basic catalyst in order to obtain high disulfide yields.

Basic catalysts which are suitable for the process of this invention are inorganic bases or organic amines. Examples of inorganic bases are ammonia and sodium carbonate. Examples of organic amines are those containing 1 to 10 carbon atoms, preferably tertiary amines, such as ethanolamine, N,N-dimethylethanolamine, triethylamine, pyridine or quinoline. The basic catalyst is usually used in the ratio of about 0.01 to 5 percent by weight of the organic sulfonyl halide, a preferred amount being about 3 weight percent.

the temperature of the reaction is generally in the range of about 50° to 200° C., preferably about 95° to 135° C. Usually, the solvents chosen have a boiling point of about 95° to 135° C so that the reaction is conducted within the temperature range of about 95° to 135° C. In the absence of a solvent, wherein the reaction is carried out neat with a basic catalyst, the reaction is conducted normally at about 125° to 200° C., at a temperature chosen slightly above the melting points of either the organic sulfonyl halide or mercaptan such that the reaction mass is in the liquid state.

The time of reaction depends mainly upon the temperature employed and is generally about 5 minutes to 24 hours for a temperature range of about 50° to 200° C.

Yields of disulfides produced in reaction are generally about 50 to 100 percent of theoretical, wherein the theoretical yield is based on theoretical amount of disulfides produced from the reaction of 1 mole of sulfonyl chloride with 5 moles of mercaptan.

Methods of product recovery will of course be obvious to one skilled in the art and will depend on the physical nature of the obtained disulfide. If it is a solid, precipitation from the reaction mixture can be utilized, if it is a liquid, then the reaction mixture can be distilled to yield the desired disulfide.

The following examples are given for illustrative purposes only and are not to be construed as limitations upon the scope and spirit of the instant invention. In the examples, parts are by weight except where otherwise indicated.

EXAMPLE 1

A mixture of 150 parts (0.6 mol) of 2,5-dichlorobenzenesulfonyl chloride, 550 parts (3.0 mols) of 2,5-dichlorobenzenethiol and 310 parts (2.6 mols) of sulfolane were mixed together and heated for 3 hours at 95° C. ± 5° C. while stirring. Two liquid layers separated at the end of the reaction. The upper layer consisted of water, hydrochloric acid (reaction by-products) and sulfolane. The lower layer contained product plus some solvent. The layers were separated and the lower layer was diluted with an equal amount of acetone. After cooling to about 15° to 25° C, the mixture was filtered, and resulting solid washed with acetone to recover 575 parts (1.6 mols) of 2,5-dichlorobenzene disulfide (90 percent of theory). The remaining 10 percent of product disulfide was recovered from the acetone - sulfolane layer by additional workup. The purity of the product as determined by gas chromatography versus a standard sample was 99 percent. No detectable sulfinic acid was observed.

EXAMPLE 2

A mixture of 30 parts (0.122 mol) of 2,5-dichlorobenzenesulfonyl chloride, 110 parts (0.62 mol) of 2,5-dichlorobenzenethiol and 31 parts (0.245 mol) of sulfolane were heated for 2 hours at 95° C. ± 5° C. The product 2,5-dichlorobenzene disulfide was recovered by the method of Example 1 and corresponded to 96 percent of theory. The product purity was 97 percent as determined by gas chromatography, with no detectable sulfinic acid being present.

EXAMPLE 3

A mixture of 30 parts (0.122 mol) of 2,5-dichlorobenzenesulfonyl chloride, 110 parts (0.62 mol) of 2,5-dichlorobenzenethiol and 14.7 parts (0.319 mol) of ethanol were mixed together and heated for 3 hours at 80° to 85° C. A 76.5 percent theoretical yield of 2,5-dichlorobenzene disulfide of 99 percent purity was recovered using the procedure of Example 1.

EXAMPLE 4

A mixture of 30 parts of 2,5-dichlorobenzenesulfonyl chloride, 110 parts of 2,5-dichlorobenzenethiol and 23 parts of dimethylformamide was heated for 3 hours at 95° ± 5° C. A 97 percent theoretical yield of the corresponding 2,5-dichlorobenzene disulfide was recovered using the procedure of Example 1.

EXAMPLE 5

A mixture of 30 parts (0.122 mol) of 2,5-dichlorobenzenesulfonyl chloride, 110 parts (0.62 mol) of 2,5-dichlorobenzenethiol and 1 ml. triethylamine was heated for 3 hours at 95° to 100° C. Using the procedure of Example 1, 102 parts of pure 2,5-dichlorobenzene disulfide were recovered representing a yield of 78 percent of theory.

EXAMPLE 6

The same materials and quantities were used as in Example 5 but the reaction mixture as heated for ½ hour at 120° to 125° C. A quantitative yield (100%) of 2,5-dichlorobenzene disulfide as recovered by using the procedure of Example 1.

EXAMPLE 7

A mixture of 60 parts (0.245 mol) of 2,5-dichlorobenzenesulfonyl chloride, 260 parts (1,23 mol) of 2,5-dichlorobenzenethiol and 100 ml. (0.64 mol) of octanol was reacted for 3 hours at 95° ± 5° C. A yield of 78 percent of theory of 2,5-dichlorobenzene disulfide was recovered by the procedure of Example 1. The product purity as determined by gas chromatography was 99 percent, with no detachable sulfinic acid being present.

We claim:

1. A process for preparing organic disulfides free of sulfinic acid hich comprises reacting in the liquid phase an organic sulfonyl halide of the formula, $RSO_2X$, wherein X is a halogen and R is an organic radical selected from the group consisting of:

linear or branched alkyl radicals containing 1 to 18 carbon atoms; sutstituted benzyl radicals of the formula:

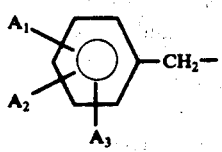

wherein the substituents $A_1$ to $A_3$ are independently selected from hydrogen, halogen and alkoxy containing 1 to 4 carbon atoms; cycloalkyl radicals containing 5 to 8 carbn atoms and 0 to 2 chlorine atoms; aromatic radicals of the formula:

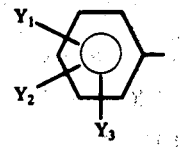

wherein $Y_1$, $Y_2$ and $Y_3$ are independently selected from hydrogen, halogen, alkyl containing 1 to 12 carbon atoms, alkoxy containing 1 to 4 carbon atoms, phenyl and a fused benzene ring formed from two adjacent Y substituents;

heterocyclic radicals of the formula:

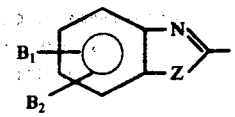

wherein Z is either oxygen, nitrogen or sulfur, and $B_1$ and $B_2$ are independently selected from hydrogen, halogen and alkoxy containing 1 to 4 carbon atoms, with a mercaptan of the formula, R'SH, wherein R' may be the same as R or different and is a member of the group as defined above for R, in a ratio of at least about 5 moles of mercaptan per mole of organic sulfonyl halide.

2. The process of claim 1 wherein the organic sulfonyl halide is an organic sulfonyl chloride.

3. The process of claim 2 wherein the organic sulfonyl chloride is a mono-, di- or trihalogenated benzenesulfonyl chloride and the mercaptan is a mono-, di- or trihalogenated aromatic mercaptan.

4. The process of claim 3 wherein the organic sulfonyl chloride is 2,5-dichlorobenzenesulfonyl chloride and the mercaptan is 2,5-dichlorobenzenethiol.

5. The process of claim 1 wherein the reaction is carried out at a temperature of about 50° to 200° C.

6. The process of claim 1 wherein the reaction is carried out in the presence of an inert polar solvent.

7. The process of claim 6 wherein the polar solvent is selected from the group consisting of monohydric aliphatic alcohols containing 1 to 8 carbon atoms, linear and cyclic alkylene sulfones containing 1 to 8 carbon atoms, N,N-dialkylalkanoylamides containing 1 to 4 carbon atoms, N-alkyl cylic lactums containing 1 to 6 carbon atoms, aliphatic ketones containng 3 to 6 carbon atoms, linear and cyclic aliphatic ethers containing 2 to 8 carbon atoms, carboxylic acids containing 1 to 4 carbon atoms, lower alkyl glycols containing 2 to 4 carbon atoms, trialkylphosphites containing 3 to 15 carbon atoms and monoalkoxyethanols containing 3 to 6 carbon atoms.

8. The process of claim 1 wherein the reaction is carried out in the presence of a basic catalyst.

9. The process of claim 8 wherein the catalyst is an organic amine.

10. The process of claim 9 wherein the reaction is carried out in the presence of about 0.01 to 5 weight percent of an organic amine based on the weight of the sulfonyl halide.

11. The process of claim 10 wherein the organic sulfonyl halide is 2,5-dichlorobenzenesulfonyl chloride, the mercaptan is 2,5-dichlorobenzenethiol and the organic amine is triethylamine.

* * * * *

UNITED STATES PATENT OFFICE
CERTIFICATE OF CORRECTION

Patent No. 4,069,259    Dated January 17, 1978

Inventor(s) Divna Cipris and Dirk Pouli

It is certified that error appears in the above-identified patent and that said Letters Patent are hereby corrected as shown below:

Col. 1, line 23, "methd" should be -- method --.

line 42, "JACS 74," should be -- JACS $\underline{74}$, --.

line 50, underline "Gibson" through "Smiles".

line 51, underline "127".

Col. 2, line 55 "This" should be -- The --.

Col. 3, line 17, "octadecylmetcaptan" should be
       -- octadecylmercaptan --.

Col. 4, line 5, insert a comma at end of line.

line 6, delete comma at beginning of line.

line 47, "an" should be -- and --.

line 49, "an" should be -- and --.

Col. 5, line 39, "the" (first occurrence) should be -- The --.

Col. 7, line 11, "detachable" should be -- detectable --.

UNITED STATES PATENT OFFICE
CERTIFICATE OF CORRECTION

Patent No. 4,069,259  Dated January 17, 1978

Inventor(s) Divna Cipris and Dirk Pouli

It is certified that error appears in the above-identified patent and that said Letters Patent are hereby corrected as shown below:

IN THE CLAIMS

Col. 7, line 16, (claim 1), "hich" should be -- which --.

Col. 7, line 36 (claim 1), "carbn" should be -- carbon --.

Col. 8, line 34 (claim 7), "lactums" should be -- lactams --.

Signed and Sealed this

Eleventh Day of July 1978

[SEAL]

Attest:

RUTH C. MASON
Attesting Officer

DONALD W. BANNER
Commissioner of Patents and Trademarks